US012776202B2

(12) United States Patent
Ku

(10) Patent No.: US 12,776,202 B2
(45) Date of Patent: Oct. 27, 2026

(54) METHOD OF PROVIDING BIOMETRIC INFORMATION

(71) Applicant: I-SENS, INC., Seoul (KR)

(72) Inventor: Ye Sol Ku, Seoul (KR)

(73) Assignee: I-SENS, INC., Seoul (KR)

( * ) Notice: Subject to any disclaimer, the term of this patent is extended or adjusted under 35 U.S.C. 154(b) by 1 day.

(21) Appl. No.: 19/047,590

(22) Filed: Feb. 6, 2025

(65) Prior Publication Data

US 2025/0308378 A1 Oct. 2, 2025

(30) Foreign Application Priority Data

Mar. 29, 2024 (KR) ........................ 10-2024-0043045

(51) Int. Cl.

| | |
|---|---|
| ***G08C 25/00*** | (2006.01) |
| ***A61B 5/00*** | (2006.01) |
| ***A61B 5/145*** | (2006.01) |
| ***G16H 10/60*** | (2018.01) |
| ***G16H 40/67*** | (2018.01) |
| ***G16H 50/30*** | (2018.01) |

(52) U.S. Cl.

CPC ............ *G08C 25/00* (2013.01); *A61B 5/0004* (2013.01); *A61B 5/14503* (2013.01); *A61B 5/14532* (2013.01); *G16H 10/60* (2018.01); *G16H 40/67* (2018.01); *G16H 50/30* (2018.01)

(58) Field of Classification Search

CPC ... G08C 25/00; A61B 5/0004; A61B 5/14503; A61B 5/14532; A61B 5/0002; A61B 5/150847; A61B 5/155; A61B 5/157; G16H 10/60; G16H 40/67; G16H 50/30; H04L 67/12

See application file for complete search history.

(56) References Cited

U.S. PATENT DOCUMENTS

| | | | | |
|---|---|---|---|---|
| 9,226,702 | B2 | 1/2016 | Ecoff et al. | |
| 2017/0124350 | A1* | 5/2017 | Reihman .............. | A61B 5/0004 |
| 2023/0089907 | A1* | 3/2023 | Mandapaka ......... | A61B 5/0004 709/227 |

OTHER PUBLICATIONS

Extended European Search Report for European Patent Application No. 25156358.1, Jul. 14, 2025.

* cited by examiner

*Primary Examiner* — Brian Wilson

(74) *Attorney, Agent, or Firm* — NKL LAW; Jae Youn Kim

(57) ABSTRACT

One embodiment may provide a method of providing biometric information including receiving biometric information at a first time interval; outputting the biometric information; when an event related to data reception occurs, receiving the biometric information at a second time interval different from the first time interval; and outputting the biometric information received at the second time interval.

9 Claims, 14 Drawing Sheets

METHOD OF PROVIDING BIOMETRIC INFORMATION

CROSS-REFERENCE TO RELATED PATENT APPLICATION

The present application claims priority under 35 U.S.C. § 119 (a) to Korean patent application number 10-2024-0043045 filed on Mar. 29, 2024, in the Korean Intellectual Property Office, the entire disclosure of which is incorporated by reference herein.

BACKGROUND OF THE INVENTION

1. Field

Embodiments of the present disclosure relate to providing biometric information in a glucose monitoring system, and more specifically, to a technology for providing biometric information according to a data transmission cycle that changes when a data communication-related event occurs.

2. Description of the Related Art

Recently, with the advancement of medical technology, various medical devices that are attached to a user's body have been developed and sold. A medical device attached to the user's body may be useful for monitoring biometric information or providing treatment by being attached to the skin of a chronic disease patient.

For example, chronic diseases such as diabetes require continuous management, and a medical device that is attached to the skin and measures glucose may be used to monitor glucose in diabetic patients. Diabetes is characterized by almost no noticeable symptoms in the early stages, but as the disease progresses, symptoms characteristic of diabetes appear, such as polydipsia, polyphagia, polyuria, weight loss, general malaise, itchy skin, and wounds on the hands and feet that do not heal and persist for a long time. As diabetes progresses further, complications such as vision impairment, high blood pressure, kidney disease, stroke, periodontal disease, muscle spasms, neuralgia, and gangrene appear. In order to diagnose diabetes and manage it to prevent it from developing into complications, systematic glucose measurement and treatment must be carried out together.

For diabetic patients and people who have not developed diabetes but have more sugar than normal detected in their blood, many medical device manufacturers provide various types of glucose meters that may measure glucose.

There are two types of glucose meters, one where the user collects blood from the fingertip and measures glucose on a one-time basis, and one where the user attaches it to the stomach, arm, etc., and continuously measures glucose.

In the case of diabetic patients, they generally go back and forth between hyperglycemia and hypoglycemia, and emergency situations occur during hypoglycemia, and loss of consciousness or prolonged hypoglycemia without sugar supply may result in death. Therefore, immediate detection of hypoglycemia is very important for diabetic patients, but glucose meters that measure glucose intermittently have limitations in accurately detecting this condition.

Recently, to overcome these limitations, a continuous glucose monitoring system (CGMS), which is inserted into the human body and measures glucose levels at intervals of several minutes, has been developed and used. In order to minimize the user's pain and resistance following blood collection, the CGMS may measure glucose continuously after inserting a needle-shaped transdermal sensor into areas where pain is relatively less, such as the stomach, arm, etc.

The CGMS includes a sensor transmitter that is inserted into the user's skin to measure glucose in the body and transmit the measured glucose level, and a terminal that outputs the received glucose level.

The terminal that communicates with the sensor transmitter in the CGMS transmits and receives glucose information wired or wirelessly, and the terminal must continuously receive data packets containing glucose information from the sensor transmitter. However, if the terminal fails to continuously receive glucose information from the sensor transmitter due to a temporary communication interruption between the sensor transmitter and the terminal or the user's inexperienced actions, or if the sensor transmitter and the terminal are separated from each other by a distance that prevents them from communicating with each other for a considerable period of time, the terminal may fail to receive the user's glucose information during that time. In addition, the sensor transmitter may be reset due to external stimulation to the sensor transmitter or internal configuration settings. If the sensor transmitter is reset for any reason, data containing glucose information to be sent to the terminal may be damaged or lost.

In such a case, the terminal may not be able to provide glucose information to the user in real time, which may cause a problem in which the user may not be able to properly respond to glucose changes. Accordingly, even if an event related to data containing glucose information occurs between the terminal and the sensor transmitter, the data needs to be stably transmitted from the sensor transmitter to the terminal.

SUMMARY OF THE INVENTION

Against this background, one object of embodiments of the present disclosure is to enable a terminal that transmits and receives data to and from a sensor transmitter at regular intervals to obtain biometric information from the sensor transmitter at varied intervals and provide it to a user even when an event related to data reception occurs.

In addition, another object of embodiments of the present disclosure is to enable the terminal to obtain biometric information from the sensor transmitter at a changed cycle and provide it to the user even when a communication failure or reset occurs.

In order to achieve the above described objects, an embodiment may provide a method of providing biometric information, the method including: receiving biometric information at a first time interval; outputting the biometric information; when an event related to data reception occurs, receiving the biometric information at a second time interval different from the first time interval; and outputting the biometric information received at the second time interval.

In the method, the receiving of the biometric information at the first time interval and the receiving of the biometric information at the second time interval may include receiving, by a terminal, the biometric information in response to an advertisement message transmitted by a sensor transmitter at each advertisement timing.

In the method, the event may include communication failure, and the receiving of the biometric information at the second time interval may include, when the communication failure occurs, as data reception is stopped, outputting a blank space indicating presence of unreceived data by a terminal; when the communication failure is resolved, receiving the unreceived data to fill the blank space; outputting the unreceived data; and receiving the biometric information from a sensor transmitter after the second time interval as the data reception is resumed.

In the method, the receiving of the unreceived data may include receiving the unreceived data in order to fill the blank space at an advertisement timing which arrives first after the communication failure is resolved.

In the method, the second time may be shorter than the first time.

In the method, the event may include a reset which causes data to be lost from a sensor transmitter, and the receiving of the biometric information at the second time interval may include, if the reset occurs after the biometric information is output and before next biometric information is output, waiting until the biometric information is received after the reset; and receiving the biometric information after waiting for a predetermined period of time.

In the method, the predetermined period of time may correspond to the first time, and the receiving of the biometric information after waiting for the predetermined period of time may include receiving the biometric information after the first time from a time point of the reset.

In the method, the second time may be longer than the first time.

In the method, the receiving of the biometric information at the first time interval and the receiving of the biometric information at the second time interval may include receiving, by a terminal, the biometric information in response to an advertisement message transmitted by the sensor transmitter at each advertisement timing, and the advertisement timing may be reset from a time point of the reset.

As described above, according to the embodiments, even when an event related to data reception occurs, the terminal may stably receive biometric information from the sensor transmitter by changing a data transmission cycle.

In addition, according to the embodiments, even when a communication failure event occurs, the biometric information measured during the period of communication failure may be provided to the user without loss by receiving unreceived data and changing the data transmission cycle to re-receive the biometric information.

DETAILED DESCRIPTION

In describing the present disclosure, if it is determined that related known functions may unnecessarily obscure the gist of the present disclosure as they are obvious to those skilled in the art, detailed descriptions thereof will be omitted.

The terms used in the present application are used merely to describe particular embodiments and are not intended to limit the present disclosure. Singular expressions include plural expressions unless the context clearly indicates otherwise. In the present application, it should be understood that terms such as "comprise", "include", or "have" are intended to designate the presence of features, numbers, steps, operations, components, parts, or combinations thereof described in the specification, and they do not preclude the possibility of the presence or addition of one or more other features, numbers, steps, operations, components, parts, or combinations thereof.

Terms such as first and second are merely identifiers used to distinguish identical or corresponding components, and the identical or corresponding components are not limited by terms such as first and second.

Hereinafter, embodiments according to the present disclosure will be described in detail with reference to the accompanying drawings, and in describing with reference to the accompanying drawings, identical or corresponding components will be assigned the same drawing numbers and overlapping descriptions thereof will be omitted.

Figure 1:
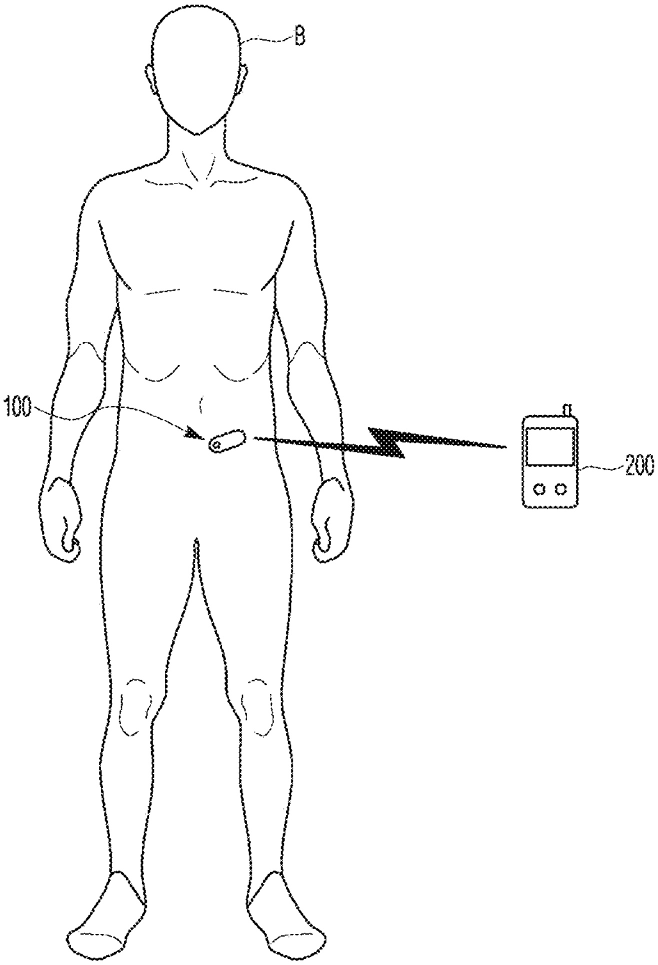
FIG. 1 is a diagram for schematically explaining a glucose monitoring system according to an embodiment.

FIG. 1 is a diagram for schematically explaining a glucose monitoring system according to an embodiment.

Referring to FIG. 1, a glucose monitoring system 10 (hereinafter referred to as a "system") according to an embodiment may include a sensor transmitter 100 and a terminal 200.

The sensor transmitter 100 is attached to a human body B, and when the sensor transmitter 100 is attached to the human body B, one end of a sensor of the sensor transmitter 100 is inserted into the skin to periodically extract body fluids from the human body and measure glucose.

The terminal 200 may receive a biosignal including glucose information from the sensor transmitter 100, generate glucose information from the biosignal, and output to the user. The terminal 200 may include, but is not limited to, various devices such as smartphones, mobile phones, tablet PCs, desktops, and laptops, and may have a communication interface capable of communicating with the sensor transmitter 100 and may include a device on which a program or application may be installed.

The sensor transmitter 100 may periodically transmit measured biosignals to the terminal 200 at the request of the terminal 200 or at a set time. For data communication between the sensor transmitter 100 and the terminal 200, the sensor transmitter 100 and the terminal 200 may be connected to each other via a wired connection such as a USB cable or wirelessly using methods such as infrared communication, NFC communication, or Bluetooth.

Figure 2:
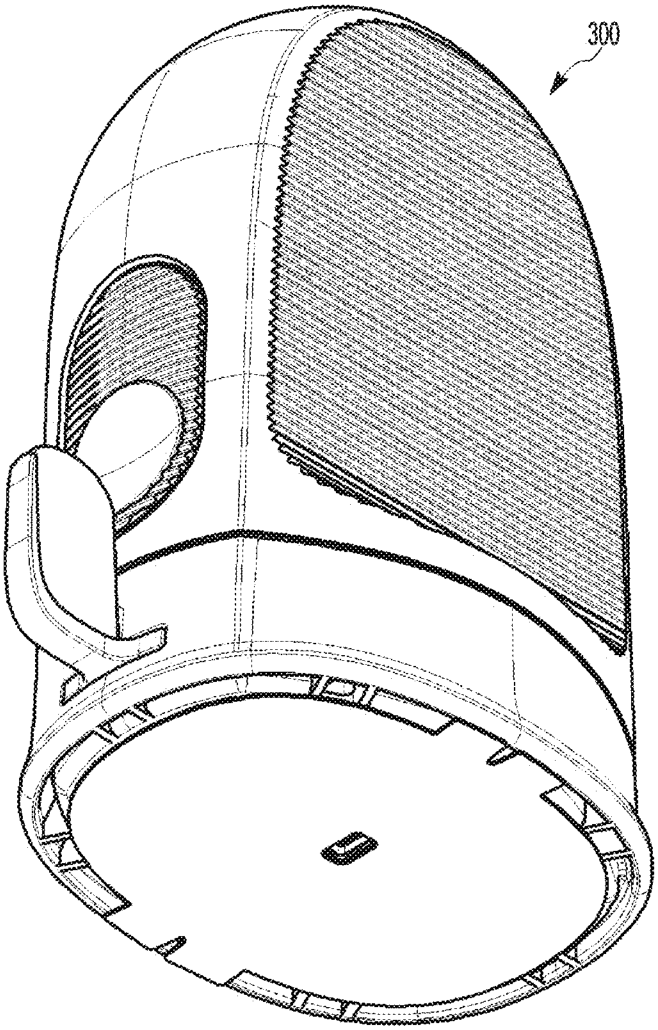
FIG. 2 is a diagram for explaining an applicator for attaching a sensor transmitter to a human body according to an embodiment.
Figure 3:
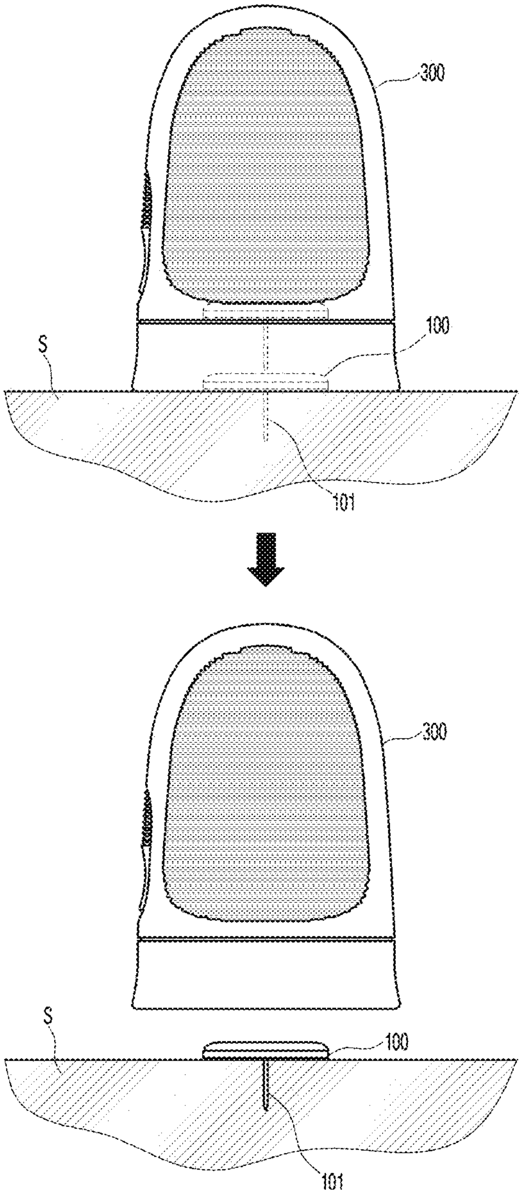
FIG. 3 is a diagram for explaining a process of attaching a sensor transmitter to a human body using an applicator according to an embodiment.

FIG. 2 is a diagram for explaining an applicator for attaching a sensor transmitter to a human body according to an embodiment, and FIG. 3 is a diagram for explaining a process of attaching a sensor transmitter to a human body using an applicator according to an embodiment.

Referring to FIGS. 2 and 3, an applicator 300 according to an embodiment has the sensor transmitter 100 inside and operates to discharge the sensor transmitter 100 to the outside and attach it to a specific body part of the user through manipulation by the user. The applicator 300 is formed in a shape with one side open, and the sensor transmitter 100 is installed in the applicator 300 through the open side of the applicator 300.

When attaching the sensor transmitter 100 to a part of the body using the applicator 300, in order to insert one end of a sensor provided in the sensor transmitter 100 into the skin, the applicator 300 may include a needle (not shown) formed to surround one end of the sensor inside, a first elastic member (not shown) that pushes the needle and one end of the sensor together into the skin, and a second elastic member (not shown) for pulling out only the needle. Through this configuration of the applicator 300, the needle and one end of the sensor may be simultaneously inserted into the skin by decompressing the first elastic member (not shown) disposed in a compressed state inside the applicator 300. When one end of the sensor is inserted into the skin, only the needle is pulled out by decompressing the compressed second elastic member (not shown). The user may safely and easily attach the sensor transmitter 100 to the skin through the applicator 300.

Looking in detail at the process of attaching the applicator 300 to the human body B, with a protective cap (not shown) removed, the open side of the applicator 300 is brought into close contact with the skin S of a specific area of the human body B. When the applicator 300 is operated in this way while the applicator 300 is in close contact with the skin S of the human body B, the sensor transmitter 100 is discharged from the applicator 300 and may be attached to the skin S. Here, one end of the sensor 101 is disposed at the lower part of the sensor transmitter 100, exposed from the sensor transmitter 100, and one end of the sensor 101 may be partially inserted into the skin S through the needle provided in the applicator 300. Therefore, the sensor transmitter 100 may be attached to the skin S with one end of the sensor 101 inserted into the skin S.

Here, an adhesive tape may be provided on the surface of the sensor transmitter 100 in contact with the human body B so that the sensor transmitter 100 may be fixedly attached to the skin S of the human body B. Therefore, when the applicator 300 is separated from the skin S of the human body B, the sensor transmitter 100 may be fixedly attached to the skin S of the human body B by the adhesive tape.

Afterwards, when power is applied to the sensor transmitter 100, the sensor transmitter 100 communicates with the terminal, and the sensor transmitter 100 may transmit biosignals including glucose information to the terminal. The sensor transmitter 100 may generate not only glucose information but also various biometric information, and hereinafter, it will be explained that glucose information is measured as an example of biometric information.

Figure 4:
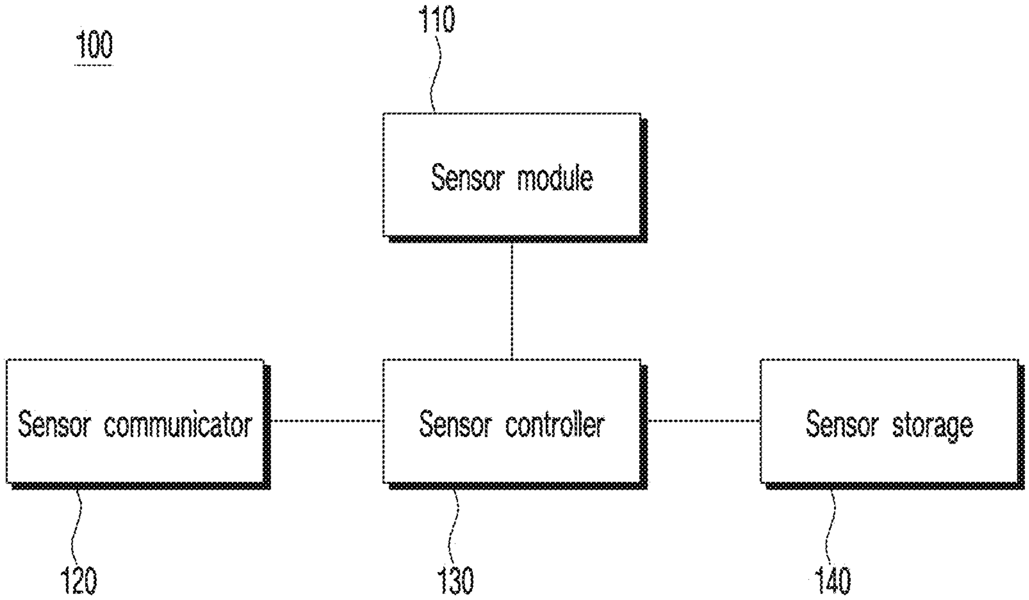
FIG. 4 is a configuration diagram of a sensor transmitter according to an embodiment.

FIG. 4 is a configuration diagram of a sensor transmitter according to an embodiment.

Referring to FIG. 4, the sensor transmitter 100 according to an embodiment may include a sensor module 110, a sensor communicator 120, a sensor controller 130, and a sensor storage 140.

The sensor module 110 may include at least one sensor that is inserted into the human body and senses biomass. At least one sensor may measure biomass and generate biosignals. The biosignal is an analog signal and may include a current value.

The sensor communicator 120 may exchange data or information with the terminal. For example, the sensor communicator 120 may transmit biosignals received from the sensor module 110 or data stored in the sensor storage 140 (for example, biometric information) to the terminal.

The sensor controller 130 may control the overall configuration of the sensor transmitter 100, including the sensor module 110, the sensor storage 140, and the sensor communicator 120. For example, the sensor controller 130 may receive a control signal from the terminal and control the configuration of the sensor transmitter 100 accordingly. In addition, the sensor controller 130 may process biosignals. For example, the sensor controller 130 may convert biosignals into analog or digital form or perform processing to remove noise as needed.

Data or information may be stored in the sensor storage 140. For example, the sensor storage 140 may store data on biomass measured by the sensor module 110, for example, the current value of the biosignal or its digital form data, or data received from the terminal, for example, the command value of the control signal.

Figure 5:
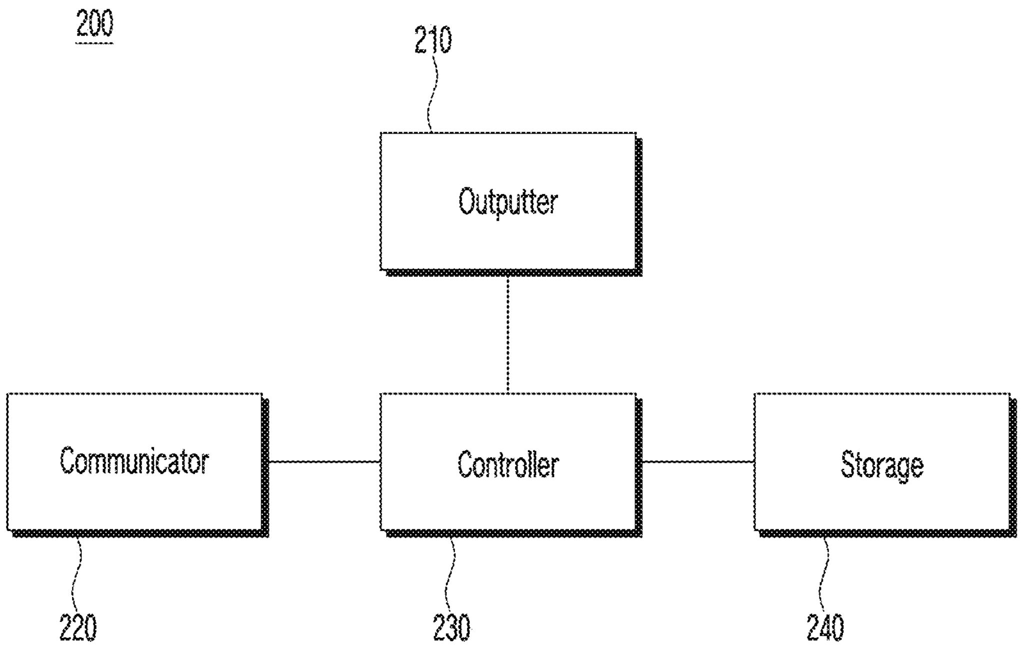
FIG. 5 is a configuration diagram of a terminal according to an embodiment.

FIG. 5 is a configuration diagram of a terminal according to an embodiment.

Referring to FIG. 5, the terminal 200 according to an embodiment may include an outputter 210, a communicator 220, a controller 230, and a storage 240.

The outputter 210 may output biometric information included in the biosignal, for example, glucose information, so that the user may check it. For example, the outputter 210 may display glucose information as numerical levels (values) or a graph processed from the numerical levels.

The communicator 220 may communicate with the sensor communicator of the sensor transmitter and exchange data or information. For example, the communicator 220 may receive a biosignal containing information about biomass (i.e., biometric information) measured by the sensor transmitter. Here, the communicator 220 may receive primarily processed biosignals from the sensor transmitter. Preferably, the processed biosignal may include discrete data (discontinuous data) in which a current value, which is an analog signal, is converted into digital data. If the current value is sampled every cycle, digital discrete data may be generated. Alternatively, the communicator 220 may transmit a control signal for controlling the sensor transmitter to the sensor transmitter.

Data or information may be stored in the storage 240. For example, data received from the sensor transmitter, for example, biometric information, may be stored in the storage 240. Here, biometric information may include digital data representing current values as glucose information. Alternatively, data input from the user or environment setting data for setting the operating environment of the terminal may be stored in the storage 240.

The controller 230 may include at least one processor that executes a program that provides notification of an event in a glucose monitoring system and at least one memory in which the program is stored. The memory and processor included in the controller 230 may be integrated into one chip or may be physically separated.

Memory may be implemented as non-volatile memory devices such as read only memory (ROM), programmable ROM (PROM), erasable programmable ROM (EPROM), electrically erasable programmable ROM (EEPROM), and flash memory, or volatile memory devices such as random access memory (RAM) to store various programs, data, and/or information.

In addition, the controller 230 may generate a glucose value, which is quantified glucose information, from biometric information. To this end, the controller 230 may obtain biometric information in the form of a current value from the sensor transmitter, and preprocess and/or process the current value of the biometric information. The controller 230 may first calculate the sensitivity and generate the glucose value according to this sensitivity.

Figure 6:
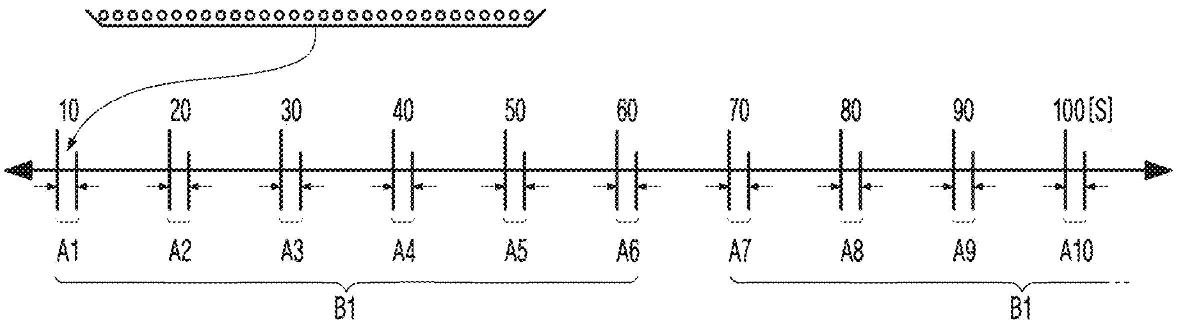
FIG. 6 is an example diagram in which biometric information is generated in a sensor transmitter or a terminal according to an embodiment.

FIG. 6 is an example diagram in which biometric information is generated in a sensor transmitter or a terminal according to an embodiment.

Referring to FIG. 6, biometric information may be generated in a sensor transmitter or a terminal according to an embodiment. Specifically, the sensor transmitter may obtain an analog (continuous) biosignal representing a current value at predetermined intervals, and sample the biosignal to generate digital (discontinuous) data representing the current value. The generated data may be processed in the sensor transmitter or the terminal to generate biometric information. Hereinafter, it is described that biometric information is generated by generating digital data from a biosignal in the sensor transmitter and processing the digital data in the terminal, but is not limited thereto, and part or all of the processing may be performed in the sensor transmitter depending on the embodiment.

For example, the sensor transmitter may obtain a biosignal in an analog form, for example, a current value, measure the biosignal every 10 seconds, and process the measured biosignal to generate a single first data. Specifically, the sensor transmitter may measure (sample) a biosignal 30 times every 10 seconds and generate digital data. The sensor transmitter may remove upper data and lower data from the 30 pieces of data, calculate an average value (A1) of the remaining data, and determine this average value (A1) as the single first data. The first data, which is the data of the average value (A1) calculated in this way, is generated in 10 second-units, and as illustrated, six average values (A1 to A6), i.e., six pieces of first data, may be generated in 1 minute.

In addition, the sensor transmitter may collect 30 pieces of first data for 300 seconds (5 minutes) and transmit them to the terminal. The terminal may receive and process 30 pieces of first data from the sensor transmitter every 300 seconds (5 minutes).

The terminal may generate an average value (B1) again using the six pieces of first data (average values (A1 to A6)). In generating the average value (B1), the terminal may remove the upper data and lower data among the six average values (A1 to A6) and generate the average value (B1) of the remaining data. Second data, which is the data of the average value (B1) calculated in this way, is generated in 1 minute-units, and as illustrated, one average value (B1), i.e., 1 piece of second data, may be generated in 1 minute. As described above, in some cases, processing into the second data may also be performed in the sensor transmitter.

Figure 7:
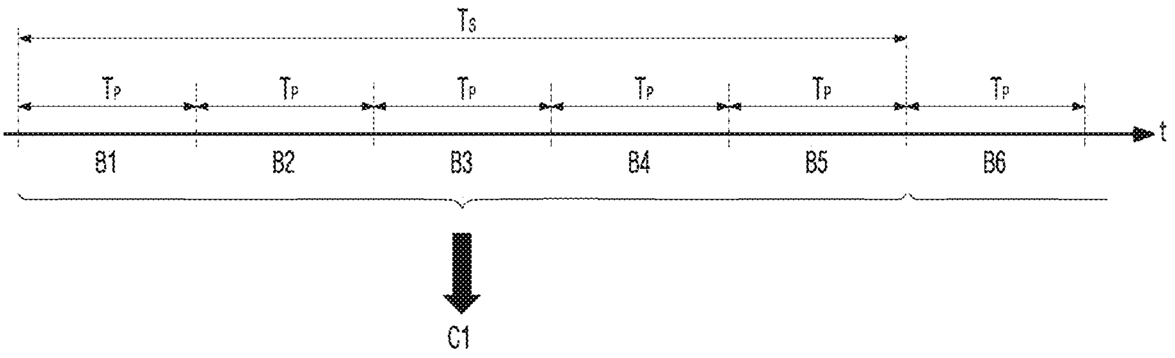
FIG. 7 an example diagram in which a data packet is generated in a sensor transmitter or a terminal according to an embodiment.

FIG. 7 an example diagram in which a data packet is generated in a sensor transmitter or a terminal according to an embodiment.

Referring to FIG. 7, second data may be processed to generate biometric information in a sensor transmitter or a terminal according to an embodiment. In the above-described example, the terminal may receive the 30 pieces of first data in 10 second-units from the sensor transmitter and obtain 5 pieces of second data (B1) in 1 minute-units. In addition, the terminal may generate an average value (C1) using 5 pieces of second data (average values (B1 to B5)). In generating the average value (C1), the terminal may remove upper data and lower data among the 5 average values (B1 to B5) and generate an average value (C1) of the remaining data. Third data, which is the data of the average value (C1) calculated in this way, is generated in 5-minute units, and as illustrated, one average value (C1), i.e., 1 piece of third data, may be generated in 5 minutes. As described above, in some cases, processing into third data may be performed in the sensor transmitter.

Here, the terminal may sequentially generate second data (B1 to B5) during a biometric information generation period (Tp) and generate one third data (C1) during a glucose value biometric information generation period (Ts). In the glucose value biometric information generation period (Ts), a glucose value is calculated from the third data (C1) through sensitivity, and in the biometric information generation period (Tp), second data (B1 to B5) that serve as the basis for the third data (C1) may be generated. In the example described above, the biometric information generation period (Tp) may correspond to 1 minute, and the glucose value biometric information generation period (Ts) may correspond to 5 minutes.

In this way, the third data generated in 5-minute units may undergo a noise removal process by a filter. The filtered third data may be converted into biometric information including a glucose value by applying sensitivity, and such biometric information may be output to the user.

Figure 8:
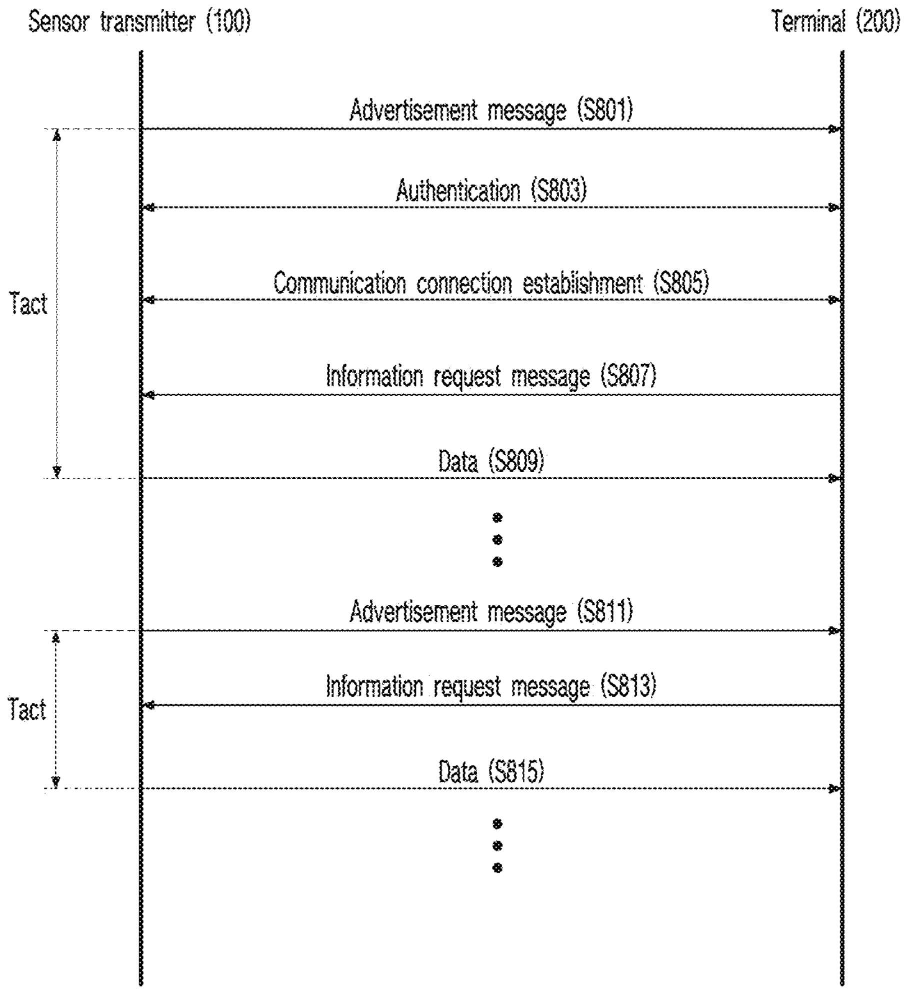
FIG. 8 is a flowchart for explaining a method of transmitting and receiving biometric information between a sensor transmitter and a terminal according to an embodiment.

FIG. 8 is a flowchart for explaining a method of transmitting and receiving biometric information between a sensor transmitter and a terminal according to an embodiment.

Referring to FIG. 8, the sensor transmitter 100 and the terminal 200 according to an embodiment may connect communication in order to transmit and receive data including biometric information. Data may be transmitted and received after the communication connection. The sensor transmitter 100 and the terminal 200 may be connected to each other through wired or wireless communication, and may connect communication in a manner such as USB communication, infrared communication, Bluetooth communication, etc.

Specifically, the sensor transmitter 100 and the terminal 200 may transmit and receive differently depending on whether communication is disconnected and a new communication is connected (when connecting initial communication) or only data is transmitted and received after initial communication is connected. First, in a state of communication disconnection, when the sensor transmitter 100 and the terminal 200 establish a new communication connection, the sensor transmitter 100 may transmit an advertisement message to the terminal 200 (step S801). The sensor transmitter 100 may periodically transmit an advertisement message to the terminal 200, and this process may be called advertisement. The terminal 200 may receive the advertisement message and perform authentication with the sensor transmitter 100 (step S803). For example, the sensor transmitter 100 and the terminal 200 may authenticate that they are valid devices through a hash value. Then, the sensor transmitter 100 and the terminal 200 may establish a communication connection (step S805). The communication connection is a state in which data may be transmitted and received immediately without going through a separate initial communication process such as authentication, and the sensor transmitter 100 and the terminal 200 may transmit and receive data in response to an advertisement message at any time while the communication connection is being established. The terminal 200 may transmit an information request message to the sensor transmitter 100 to obtain data including biometric information (for example, 30 pieces of first data) (step S807). The sensor transmitter 100 that has received the information request message may transmit data including biometric information (for example, 30 pieces of first data) to the terminal 200 in response thereto (step S809).

Once the initial communication is connected, data may be transmitted and received in the communication connection establishment state without a separate authentication process. The sensor transmitter 100 may transmit an advertisement message to the terminal 200 periodically or aperiodically (step S811). The terminal 200 may send an information request message requesting data transmission in response to the advertisement message to the sensor transmitter 100 (step S813). The sensor transmitter 100 may transmit data in response to the information request message (step S815).

Here, the terminal 200 receives data from the sensor transmitter 100 from time to time, but the terminal 200 may receive data in response to the advertisement message only when the sensor transmitter 100 transmits the advertisement message. The sensor transmitter 100 may send this advertisement message to the terminal 200 periodically or aperiodically, and the terminal 200 may request and receive data accordingly. In addition, the sensor transmitter 100 may not continuously send the advertisement message, but may transmit it only in active mode, i.e., while awake. Accordingly, data transmission and reception between the sensor transmitter 100 and the terminal 200 may be performed only during this active mode period (Tact). The sensor transmitter 100 may stand by without sending any data during the inactive mode, i.e, the non-active mode period.

In addition, the terminal 200 may determine whether there is unreceived data through the information request message. Since data including biometric information (or a data packet) is assigned an identifier, the terminal 200 may determine whether it has received data from the sensor transmitter 100 through this identifier. For example, biometric information received from the sensor transmitter 100 may be stored in the storage of the terminal 200 and output sequentially. The biometric information is assigned an identifier by the sensor transmitter 100, and this identifier may be a serial number assigned according to the order in which the biometric information is generated by the sensor transmitter 100. The terminal 200 may determine the total number of biometric information received by the terminal 200 through the last identifier of the stored biometric information. The sensor transmitter 100 may also calculate the total number of biometric information to be transmitted to the terminal 200 through the last identifier of the stored biometric information. The sensor transmitter 100 may continuously generate biometric information and assign an identifier to the biometric information regardless of the communication connection with the terminal 200. When the sensor transmitter 100 starts communication with the terminal 200, the sensor transmitter 100 may sequentially send to the terminal 200 biometric information after the last identifier of the biometric information transmitted to the terminal 200. The terminal 200 receives all of the biometric information from the sensor transmitter or when the active mode period (Tact) during which communication is possible ends, the terminal 200 may end communication with the sensor transmitter 100.

Figure 9:
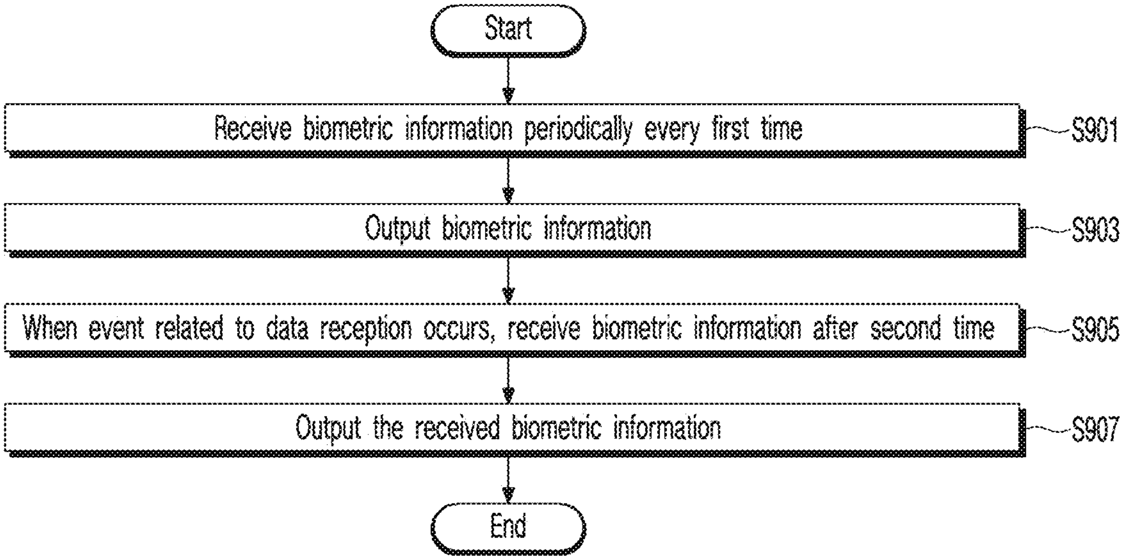
FIG. 9 is a flowchart for explaining a method of providing biometric information based on a changing data transmission cycle by a terminal according to an embodiment.
Figure 10:
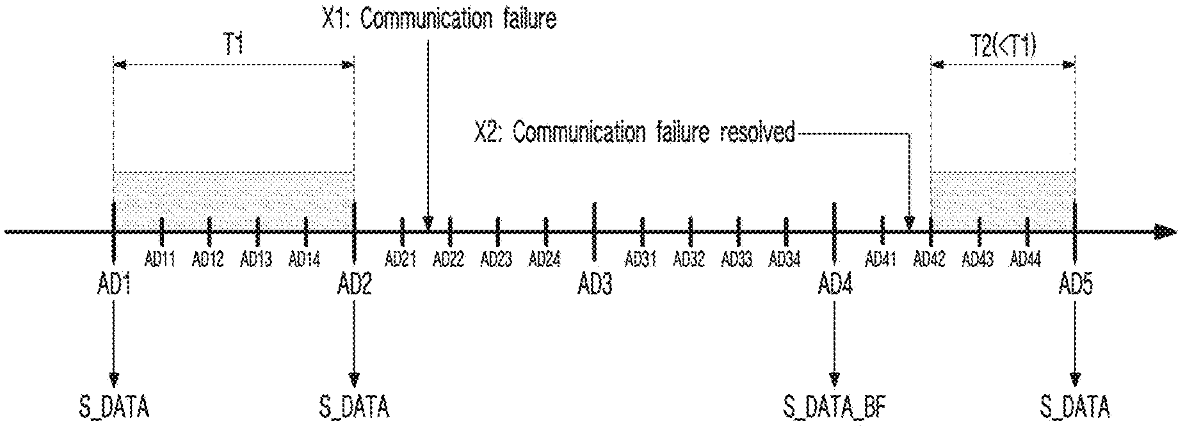
FIG. 10 is a diagram for explaining an example of a method of providing biometric information based on a changing data transmission cycle by a terminal according to an embodiment.
Figure 11:
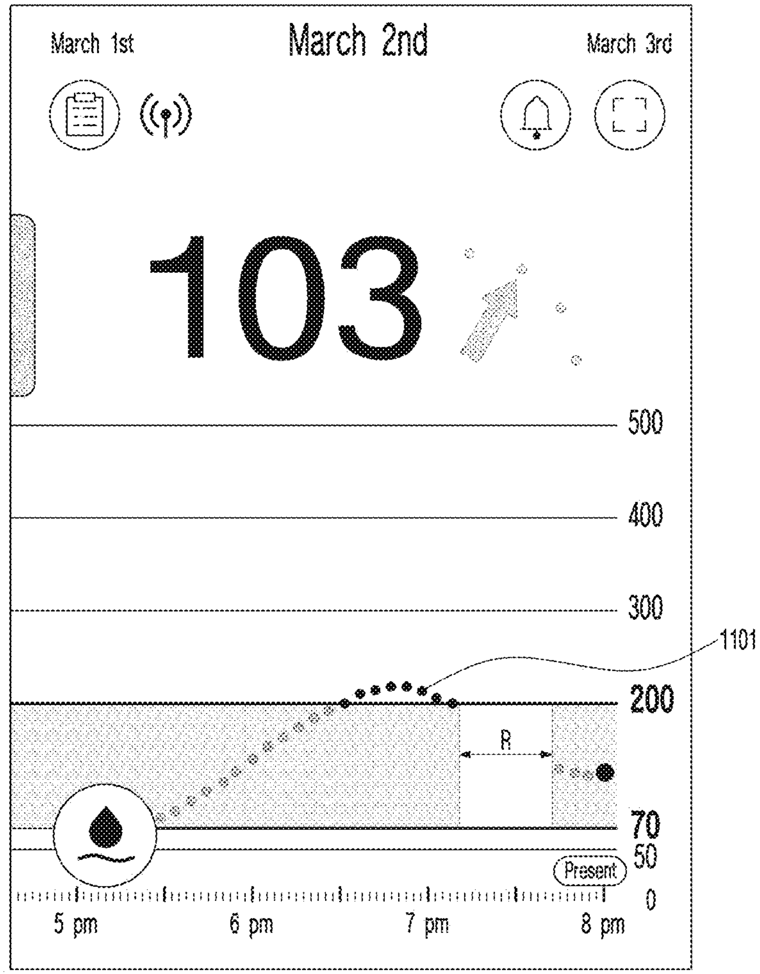
FIG. 11 is an example diagram of a user interface provided by a terminal to provide biometric information based on a changing data transmission cycle according to an embodiment.

FIG. 9 is a flowchart for explaining a method of providing biometric information based on a changing data transmission cycle by a terminal according to an embodiment, FIG. 10 is a diagram for explaining an example of a method of providing biometric information based on a changing data transmission cycle by a terminal according to an embodiment, and FIG. 11 is an example diagram of a user interface provided by a terminal to provide biometric information based on a changing data transmission cycle according to an embodiment.

Referring to FIG. 9, a method of providing biometric information based on a changing data transmission cycle by a terminal according to an embodiment may be illustrated.

The controller of the terminal may transmit and receive data with the sensor transmitter through the communicator.

The controller of the terminal may receive data including biometric information from the sensor transmitter periodically at a regular time interval (i.e., a first time) through the communicator (step S901). For example, the terminal may receive an advertisement message transmitted by the sensor transmitter at each advertisement timing, and may send an information request message in response thereto and receive biometric information. The sensor transmitter may send an advertisement message at a predetermined time interval, and the advertisement timing may be understood as the time at which the advertisement message is sent. The interval at which the controller of the terminal receives the biometric information is the first time, and the first time is the interval of the advertisement timing, and the advertisement timing may be repeated in the cycles of the first time. In normal times, the controller of the terminal may receive the biometric information at the advertisement timing that is repeated every first time.

In addition, the outputter of the terminal may output the biometric information (step S903). The biometric information may be received at the first time interval and output at the first time interval by the outputter at the same time.

While the terminal receives the biometric information from the sensor transmitter and outputs it to the user, an event related to the data reception of the terminal may occur. When the event occurs, the terminal may receive the biometric information from the sensor transmitter after a second time that is different from the first time (step S905). Even in the process of receiving after the second time, the terminal may receive the biometric information in response to the advertisement message sent by the sensor transmitter at the advertisement timing. When the event occurs, the terminal cannot receive biometric information from the sensor transmitter due to the event and thus cannot output it to the user. Afterwards, when the event is resolved or time passes, the terminal may start receiving biometric information from the sensor transmitter again. As a result, the terminal may receive biometric information that should have been received but was not received. In addition, the terminal may output biometric information received after the second time to the user (step S907).

Here, in the process of the terminal receiving biometric information after the second time, the period for the terminal to receive biometric information from the sensor transmitter may change. If the terminal normally received biometric information periodically at an interval of the first time before the event occurred, the terminal may receive biometric information at an interval of the second time after the event occurred. The second time is different from the first time and may be short or long. Hereinafter, a case where a communication failure occurs as an event related to data reception will be described as an example.

Referring to FIG. 10, an example of a method of providing biometric information based on a changing data transmission cycle by a terminal according to an embodiment may be illustrated. In this example, an event related to data reception may be a communication failure, and before the communication failure occurs, the terminal receives biometric information at an interval of the first time (T1), but after the communication failure occurs and is resolved, the terminal may receive biometric information at an interval of the second time (T2). The second time (T2) may be shorter than the first time (T1).

Specifically, the terminal may receive biometric information from the sensor transmitter at every first time (T1). Normally, the terminal may receive biometric information (S_DATA) from the sensor transmitter in response to an advertisement message sent by the sensor transmitter at an advertisement timing (AD1, AD2).

A communication failure may occur at time point X1 during communication between the sensor transmitter and the terminal. Here, the communication failure may mean a state in which data cannot be received due to a communication module (e.g., a Bluetooth communication module) being turned off or due to any failure (e.g., when the distance between the sensor transmitter and the terminal increases) even when the communication module is turned on. The former example corresponds to a case in which the communication connection between the sensor transmitter and the terminal is cut off, and the latter example corresponds to a case in which the terminal stops receiving data from the sensor transmitter while the communication connection is established. The terminal may determine whether there is a communication failure based on the operating status of the communication module and whether data is received. Data reception is stopped and the terminal may output a blank space indicating the presence of unreceived data through the user interface.

If a communication failure occurs, the terminal may not receive an advertisement message even if the sensor transmitter transmits an advertisement message to the terminal. Alternatively, even if the advertisement message reaches the terminal, the terminal may not be able to transmit the information request message or receive data including biometric information in response to the information request message. At the time point when the sensor transmitter advertises, i.e., at the advertisement timing (AD3, AD4), each terminal may not be able to receive data from the sensor transmitter for the above reasons.

The advertisement timings (AD1, AD2, AD3, AD4, AD5) may be periodic or aperiodic. When the advertisement timings (AD1, AD2, AD3, AD4, AD5) are periodic, the advertisement timings (AD1, AD2, AD3, AD4, AD5) may be formed at intervals of 5 minutes (300 seconds). As in the example of the data packet described above, in principle, the sensor transmitter may send 30 pieces of collected data to the terminal at once at each advertisement timing (AD1, AD2, AD3, AD4, AD5). Advertisement timings (AD1, AD2, AD3, AD4, AD5) are repeated, and other advertisement timings may be formed at 5-minute intervals thereafter. Here, advertisement timings (AD1, AD2, AD3, AD4, AD5) may be named as the first to fifth advertisement timings, respectively. However, if a communication failure occurs, data reception is stopped, so the terminal may not receive biometric information at advertisement timings (AD3, AD4). While biometric information is not received, the terminal may output a blank space or gap where a glucose value is not displayed on the user interface.

Referring to FIG. 11, an example of a user interface in which the terminal displays a blank space due to unreceived data in this example may be illustrated. The controller of the terminal may execute an application, and the outputter may visually display a user interface implemented by the application. The outputter may obtain biometric information from the controller and display it on the user interface.

The user interface may include an icon including biometric information and a convenient function for providing the same. For example, the icon may indicate a communication state, for example, a Bluetooth communication connection. For example, the icon may indicate a smooth communication state (where a communication connection is established and biometric information is received) as blue, indicate a state in which the terminal does not receive biometric information for a predetermined period of time (a case in which a communication connection is established but biometric information is not received) as red, and indicate a state in which the communication module is turned off or is not connected to the sensor for communication (a case in which no communication connection is established) as gray. Therefore, when the communication module is turned off, the icon may turn gray.

In addition, the user interface may include a trend 1101 in order to indicate biometric information. The terminal receives and outputs biometric information from the sensor transmitter at regular intervals, and this biometric information may be output at each interval to form a kind of pattern, i.e., a trend 1101. The trend may have a form similar to a graph. The trend 1101 may be expressed over an area consisting of the highest and lowest glucose values. If data is not received by the terminal due to a communication failure, data may not be output during that period. An area where the unreceived data appears (i.e., a blank space (R)) may exist in the trend 1101. When the communication failure is resolved, data may begin to be received from the sensor transmitter to the terminal, so that biometric information may be output again.

Returning again to FIG. 10, if the communication failure is resolved at time X2 thereafter, the terminal may receive the unreceived data in order to fill the blank space at the (sub) advertisement timing (AD42) that arrives first after the communication failure is resolved starting from the time point when the communication failure is resolved, and output it to the user through the user interface (S_DATA_BF). Here, sub-advertisement timings (AD11~14, AD21~24, AD31~34, AD41~44) may be included between advertisement timings (AD1, AD2, AD3, AD4, AD5). The sub-advertisement timings (AD11~14, AD21~24, AD31~34, AD41~44) may also mean the time point when the sensor transmitter sends an advertisement message to the terminal, similar to the advertisement timings (AD1, AD2, AD3, AD4, AD5). However, in the present embodiment, it is explained that biometric information is mainly transmitted at the advertisement timings (AD1, AD2, AD3, AD4, AD5), and biometric information is not transmitted at the sub-advertisement timings (AD11~14, AD21~24, AD31~34, AD41~44) unless there are special circumstances. At sub-advertisement timings (AD11~14, AD21~24, AD31~34, AD41~44), the terminal may only receive unreceived data. The data transmission and reception operations between the terminal and the sensor transmitter at the advertisement timings (AD1, AD2, AD3, AD4, AD5) and sub-advertisement timings (AD11~14, AD21~24, AD31~34, AD41~44) are not limited thereto and may be set in various ways.

In addition, if the communication failure is resolved at time X2, the terminal may receive and output the unreceived data at the sub-advertisement timing (AD42), and therefore, the terminal may wait to receive the unreceived data until advertisement timing that arrives first after the communication failure is resolved (sub-advertisement timing (AD42)).

After the terminal receives and outputs the unreceived data, the terminal may wait to receive the biometric information until the advertisement timing (AD5) at which the biometric information may be received. Data reception is resumed and the terminal may output the unreceived data at the sub-advertisement timing (AD42) and fill in the blank space shown on the user interface with biometric information (e.g., glucose values). The terminal may wait for second time (T2) from the time point of receiving and outputting the unreceived data to the time point of receiving the biometric information. As in the advertisement timings (AD1, AD2), the terminal may receive the biometric information again at the advertisement timing (AD5). Here, the second time (T2), which is the interval at which the biometric information is received, may be shorter than the first time (T1), which is the interval at which the biometric information is normally received. Since the second time (T2) represents the period from the time point where the receiving data is received to fill the blank space until the time point where the biometric information is received normally again, when the communication failure event is resolved, the data transmission cycle may change to T2.

Figure 12:
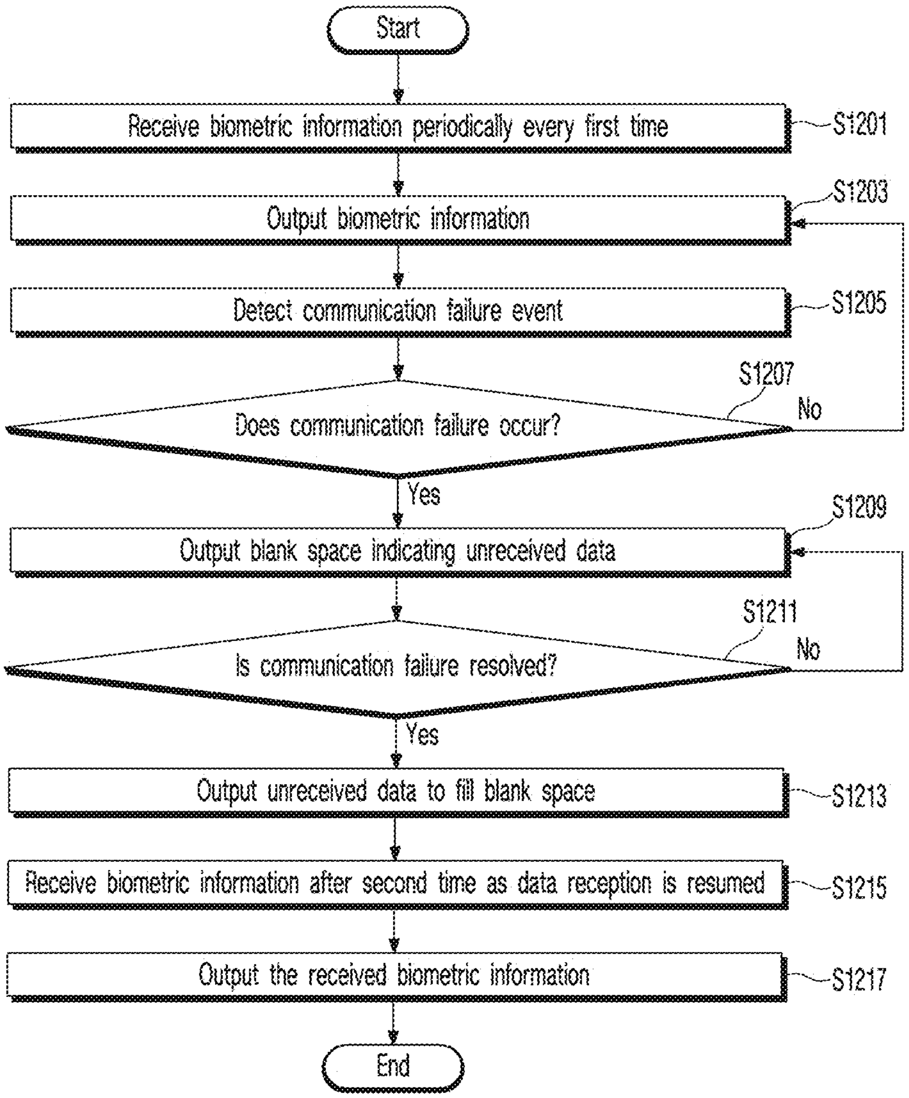
FIG. 12 is a flowchart for explaining an example of a method of providing biometric information based on a data transmission cycle by a terminal according to an embodiment.

FIG. 12 is a flowchart for explaining an example of a method of providing biometric information based on a data transmission cycle by a terminal according to an embodiment.

Referring to FIG. 12, when a communication failure occurs as an event related to data reception of a terminal according to an embodiment, the terminal may receive and output biometric information at a cycle different from the existing data transmission cycle.

The controller of the terminal may receive biometric information periodically every first time through the communicator (step S1201). In addition, the controller of the terminal may control the outputter so that the biometric information is output (step S1203).

In addition, the controller of the terminal may detect a communication failure through the communicator in order to determine whether an event such as a communication failure occurs (step S1205).

The controller of the terminal may determine whether a communication failure occurs (step S1207). If it is determined that a communication failure does not occur, the controller of the terminal may control the communicator and the outputter to continuously receive and output biometric information (NO of step S1207 and step S1203).

If it is determined that a communication failure occurs, the controller of the terminal may receive biometric information from the sensor transmitter after a second time that is different from the first time. The step of receiving biometric information after the second time may include the following steps.

The controller of the terminal may control the outputter to output a blank space indicating unreceived data during a period in which biometric information cannot be received (YES of step S1207 and step S1209).

If the communication failure is resolved in the middle, the controller of the terminal may detect and determine whether the communication failure is resolved through the communicator (step S1211). If it is determined that the communication failure is not resolved, the controller of the terminal may control the outputter to continuously output a blank space indicating unreceived data (NO of step S1211 and step S1209).

If it is determined that the communication failure is resolved, the controller of the terminal may receive the unreceived data from the sensor transmitter through the communicator. Then, the controller of the terminal may output the unreceived data to the user interface (step S1213). Alternatively, the controller of the terminal may display unoutput data among the pre-stored data as unreceived data on the user interface through the outputter.

In addition, as the communication failure is resolved and the unreceived data is output, data reception between the terminal and the sensor transmitter may also be resumed. As data reception is resumed, the terminal may receive biometric information from the sensor transmitter after the second time (step S1215). Here, the terminal may wait to receive biometric information again after receiving and outputting the unreceived data, and the biometric information (e.g., glucose values) may be displayed on the user interface after the second time from the time point where the unreceived data was output. It may be recognized by the user that biometric information is output in a cycle of second time that is shorter than the first time, which is the normal cycle.

Next, the terminal may provide the biometric information received after the second time to the user through the user interface (step S1217).

Figure 13:
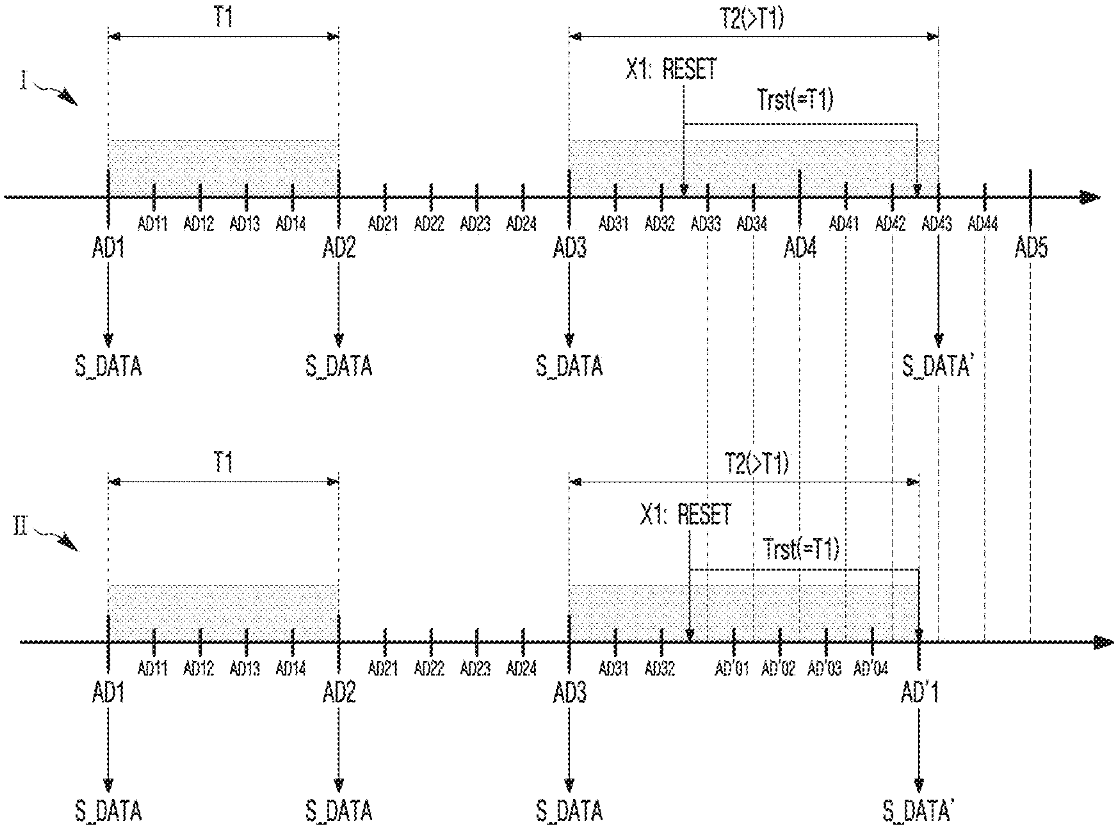
FIG. 13 is a flowchart for explaining another example of a method of providing biometric information based on a data transmission cycle by a terminal according to an embodiment.

FIG. 13 is a diagram for explaining another example of a method of providing biometric information based on a data transmission cycle by a terminal according to an embodiment.

In a process of receiving biometric information after an event related to data reception occurs in the terminal, a period during which the terminal receives biometric information from the sensor transmitter may change. If the terminal normally receives biometric information periodically at a first time interval before the event occurs, the terminal may receive biometric information at a second time interval after the event occurs. The second time is different from the first time and may be shorter or longer. Hereinafter, a case in which a sensor transmitter is reset as an event related to data reception will be explained as another example.

Referring to FIG. 13, another example of a method of providing biometric information based on a changing data transmission cycle by a terminal according to an embodiment may be illustrated. In this example, an event related to data reception may be a reset occurring in the sensor transmitter, and before the reset (RESET) occurs, the terminal receives biometric information at intervals of a first time (T1), but after the reset (RESET) occurs, the terminal may receive biometric information at intervals of a second time (T2). The second time (T2) may be longer than the first time (T1).

Specifically, the terminal may receive biometric information from the sensor transmitter at every first time (T1). Normally, the terminal may receive biometric information (S_DATA) from the sensor transmitter in response to an advertisement message sent by the sensor transmitter at advertisement timings (AD1, AD2, AD3).

During communication between the sensor transmitter and the terminal, a reset may occur in the sensor transmitter at time point X1. Here, the sensor transmitter may be reset when an external stimulus is applied to the sensor transmitter or due to a setting of an internal configuration. If the sensor transmitter is reset for any reason, data containing biometric information to be sent to the terminal may be damaged or lost. The sensor transmitter may re-measure and generate biometric information immediately after reset. In addition, the sensor transmitter may send the re-generated biometric information to the terminal according to the interval at which the biometric information is sent. In this example, the terminal and the sensor transmitter may transmit and receive data at each advertisement timing (AD1, AD2, AD3, AD4, AD5) or sub-advertisement timing (AD11~14, AD21~24, AD31~34, AD41~44).

For example (I), in which the terminal receives biometric information according to the changing data transmission cycle after the reset, the sensor transmitter may be reset at an arbitrary time point X1 between the sub-advertisement timings (AD32, AD33). The sensor transmitter may generate biometric information for one period (Trst) from that time point. Since the sensor transmitter normally generates biometric information during the first time (T1) and transmits it to the terminal, the one period (Trst) may be the same as the first time (T1). If the first time (T1) is 5 minutes, the one period (Trst) may also be 5 minutes. Since data transmission and reception between the sensor transmitter and the terminal occurs at the advertisement timing, the sensor transmitter may send biometric information at the advertisement timing (AD43) that arrives first after the one period (Trst). The terminal receives the biometric information (S_DATA') at the advertisement timing (AD43).

On the other hand, the sensor transmitter may reset the timing for sending the advertisement message from the time point of reset. In this case, the existing advertisement timings (AD4, AD5 of I) and the existing sub-advertisement timings (AD33~34, AD41~44 of I) scheduled after the reset are no longer valid, and a new advertisement timing (AD'1) and new sub-advertisement timings (AD'01, AD'02, AD'03, AD'04) may be set. For example (II), in which the sensor transmitter sets a new advertisement timing (AD'1) and new sub-advertisement timings (AD'01, AD'02, AD'03, AD'04) from the time point of reset, the sensor transmitter may be reset at an arbitrary time point X1. The sensor transmitter may generate biometric information for one period (Trst) from that time point. Since the sensor transmitter normally generates biometric information during the first time (T1) and transmits it to the terminal, the one period (Trst) may be the same as the first time (T1). The sensor transmitter may set a new advertisement timing (AD'1) and new sub-advertisement timings (AD'01, AD'02, AD'03, AD'04) by resetting or adjusting the existing advertisement timings (AD4, AD5 of I) and the existing sub-advertisement timings (AD33~34, AD41~44 of I) immediately after reset. At the new advertisement timing (AD'1), which is the time point at which the one period (Trst) ends, the sensor transmitter may transmit the biometric information generated again after reset to the terminal. The terminal receives the biometric information (S_DATA') at the new advertisement timing (AD'1). In this drawing, the difference between the existing advertisement timings (AD4, AD5) and the existing sub-advertisement timings (AD33~34, AD41~44) and the new advertisement timing (AD'1) and the new sub-advertisement timings (AD'01, AD'02, AD'03, AD'04) after the reset may be illustrated by dotted lines.

Here, the second time (T2), which is the interval at which biometric information is received, may become longer than the first time (T1), which is the interval at which biometric information is normally received. The second time (T2) may represent a period from the last time point at which biometric information was received before the reset (i.e., the advertisement timing (AD3)) to the time point at which biometric information is normally received again after the reset. When the terminal receives biometric information after the reset, the data transmission cycle may change to T2.

Figure 14:
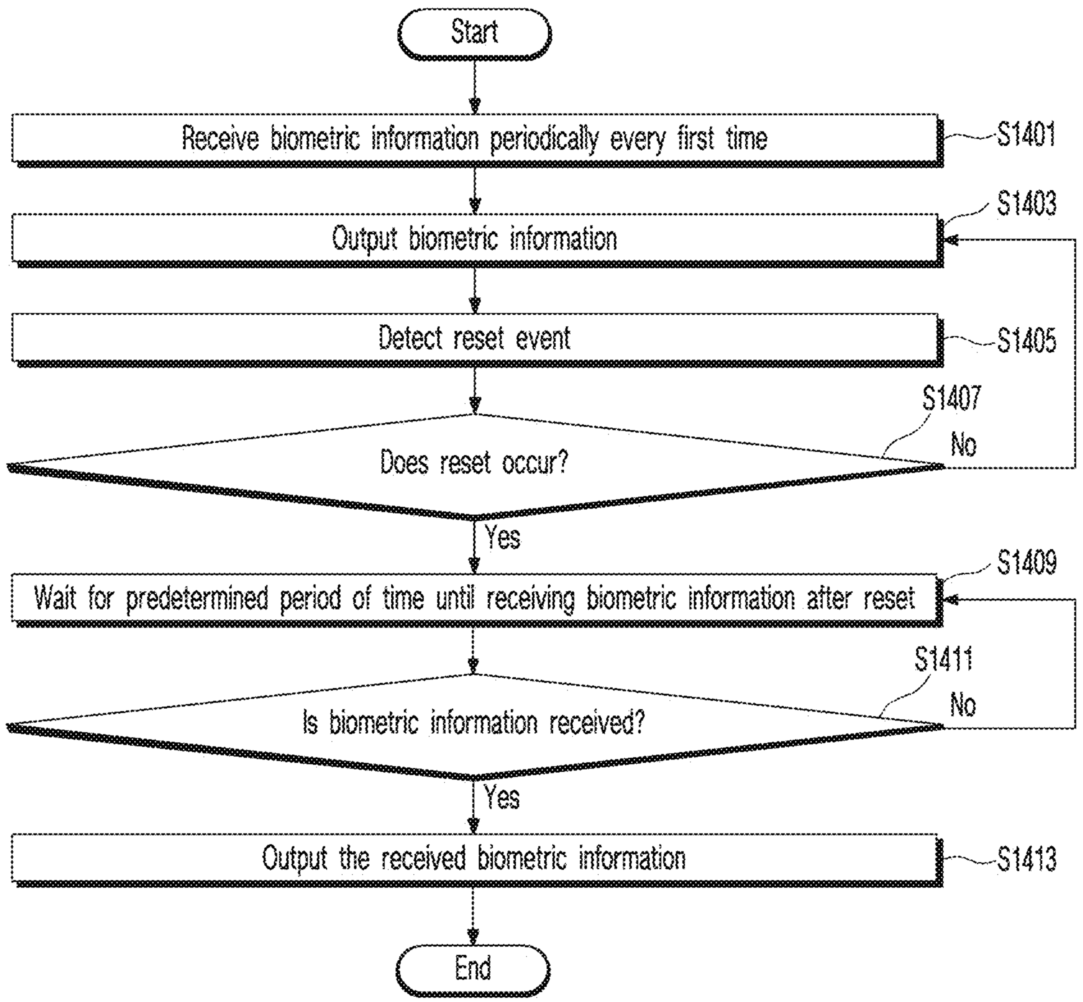
FIG. 14 is a flowchart for explaining another example of a method of providing biometric information based on a data transmission cycle by a terminal according to an embodiment.

FIG. 14 is a flowchart for explaining another example of a method of providing biometric information based on a data transmission cycle by a terminal according to an embodiment.

Referring to FIG. 14, when a reset occurs in which data is lost from a sensor transmitter as an event related to data reception of the terminal, the terminal according to an embodiment may receive and output biometric information at a cycle different from the existing data transmission cycle.

The controller of the terminal may periodically receive biometric information every first time through the communicator (step S1401). In addition, the controller of the terminal may control the outputter so that biometric information is output (step S1403).

In addition, the controller of the terminal may detect a reset event through the communicator to determine whether an event such as a reset occurs (step S1405). In addition, the controller of the terminal may determine whether a reset occurs (step S1407). For example, if the terminal does not receive data even though the data transmission cycle has arrived while the communication connection is established, the controller of the terminal may determine that the reset has occurred. Alternatively, if the reset sensor transmitter sends related information, the controller of the terminal may determine that the reset has occurred. Here, the reset may occur before the next biometric information is output after the biometric information is output from the terminal.

If it is determined that the reset does not occur, the controller of the terminal may control the communicator and the outputter to continuously receive and output biometric information (NO of step S1407 and step S1403).

If it is determined that the reset occurs, the controller of the terminal may receive biometric information from the sensor transmitter after a second time that is different from the first time. The step of receiving biometric information after the second time may include the following steps.

The controller of the terminal may wait for a predetermined period of time until receiving biometric information after the reset (step S1409). In addition, the controller of the terminal may determine whether biometric information is being received after waiting for the predetermined period of time (step S1411). When the controller of the terminal receives biometric information, the controller of the terminal may output the received biometric information (YES of step S1411 and step S1413).

Here, the predetermined period of time during which the terminal waits until receiving data may include a period from the time point of reset to after the first time, which is a period during which biometric information of one unit is generated. After the biometric information is output, a reset may occur before the next biometric information is output (between advertisement timings) and the first time may be required for generating new biometric information. Ultimately, the terminal may take the second time to receive and output the biometric information after the predetermined period of time from receiving and outputting biometric information for the last time. Therefore, the second time becomes longer than the first time. The terminal may output biometric information again after the second time from the last time point it output biometric information. It may be recognized by the user that the biometric information is output in the cycle of second time that is longer than the cycle of first time, which is the normal cycle.

If the controller of the terminal does not receive the biometric information after the predetermined period of time, the controller of the terminal may wait for a predetermined period of time until the biometric information is received (NO of step S1411 and step S1409).

The aspects of the subject matter described herein may be described in the context of computer-executable instructions, such as program modules, that are executed on a computer. Generally, program modules include routines, programs, objects, components, data structures, etc., which perform specific tasks or specific abstract data types.

Alternatively or additionally, the functionality described herein may be performed, at least in part, by one or more hardware logic components. By way of example, and not limitation, exemplary types of hardware logic components that may be used include field-programmable gate array (FPGA), program-specific integrated circuit (ASIC), application-specific standard product (ASSP), system-on-a-chip system (SOC), complex programmable logic device (CPLD), etc.

In addition, the disclosed embodiments may be implemented in the form of a non-transitory recording medium that stores programs and/or instructions executable by a computer. Instructions may be stored in the form of program code, and when executed by a processor, may create program modules to perform operations of the disclosed embodiments. The non-transitory recording medium may be implemented as a non-transitory computer-readable recording medium.

Computer-readable recording media include all types of recording media storing instructions that may be decoded by a computer. For example, there may be read only memory (ROM), random access memory (RAM), magnetic tape, magnetic disk, flash memory, optical data storage, etc.

Although embodiments of the present disclosure have been described above, those skilled in the art will be able to make various modifications and changes to the present disclosure by adding, changing or deleting components, without departing from the spirit of the present disclosure as set forth in the appended claims, which are included within the scope of rights of the present disclosure.

What is claimed is:

1. A method of providing biometric information, the method comprising:

receiving biometric information at a first time interval;

outputting the biometric information;

when an event comprising a reset, which causes data to be lost from a sensor transmitter, occurs, receiving the biometric information at a second time interval different from the first time interval; and outputting the biometric information received at the second time interval, wherein the receiving of the biometric information at the second time interval comprises:

if the reset occurs after the biometric information is output and before next biometric information is output, waiting until the next biometric information is received after the reset; and receiving the next biometric information after waiting for a predetermined period of time, and wherein, in the outputting of the biometric information received at the second time interval, the next biometric information is output after the second time interval from a time point at which the biometric information is output.

2. The method according to claim 1, wherein the receiving of the biometric information at the first time interval and the receiving of the biometric information at the second time interval comprise receiving, by a terminal, the biometric information in response to an advertisement message transmitted by the sensor transmitter at each advertisement timing.

3. The method according to claim 1, wherein the receiving of the biometric information after waiting for the predetermined period of time comprises receiving the next biometric information at an advertisement timing which arrives first after the predetermined period of time.

4. The method according to claim 1, further comprising, after the outputting of the biometric information, determining whether the reset occurs in the sensor transmitter.

5. The method according to claim 4, wherein the determining of whether the reset occurs in the sensor transmitter is performed while a communication connection between a terminal and the sensor transmitter is established.

6. The method according to claim 1, wherein the predetermined period of time is shorter than the second time interval.

7. The method according to claim 6, wherein the predetermined period of time corresponds to the first time interval, and the receiving of the biometric information after waiting for the predetermined period of time comprises receiving the biometric information after the first time interval-from a time point of the reset.

8. The method according to claim 6, wherein the second time interval is longer than the first time interval.

9. The method according to claim 1, wherein the receiving of the biometric information at the first time interval and the receiving of the biometric information at the second time interval comprise receiving, by a terminal, the biometric information in response to an advertisement message transmitted by the sensor transmitter at each advertisement timing, and the advertisement timing is reset from a time point of the reset.

* * * * *